(12) United States Patent
Van Heerde

(10) Patent No.: US 8,809,006 B2
(45) Date of Patent: Aug. 19, 2014

(54) HEMOSTASIS ASSAY

(75) Inventor: Waander Laurens Van Heerde, Nijmegen (NL)

(73) Assignee: Stichting Katholieke Universiteit, Nijmegen (NL)

(*) Notice: Subject to any disclaimer, the term of this patent is extended or adjusted under 35 U.S.C. 154(b) by 1128 days.

(21) Appl. No.: 11/774,843

(22) Filed: Jul. 9, 2007

(65) Prior Publication Data

US 2008/0026365 A1 Jan. 31, 2008

Related U.S. Application Data

(63) Continuation-in-part of application No. PCT/EP2006/000184, filed on Jan. 9, 2006.

(30) Foreign Application Priority Data

Jan. 7, 2005 (EP) .................................... 05075030

(51) Int. Cl.
*C12Q 1/56* (2006.01)

(52) U.S. Cl.
USPC .............................. 435/13; 435/214; 435/217

(58) Field of Classification Search
USPC ........................................... 435/13, 214, 217
See application file for complete search history.

(56) References Cited

U.S. PATENT DOCUMENTS

| | | | |
|---|---|---|---|
| 5,096,807 A | | 3/1992 | Leaback |
| 5,110,727 A | | 5/1992 | Oberhardt |
| 5,231,006 A | * | 7/1993 | Kolde .............................. 435/13 |
| 5,510,243 A | | 4/1996 | Boyd et al. |
| 6,245,548 B1 | * | 6/2001 | Ralston et al. ................ 435/214 |
| 6,899,877 B2 | * | 5/2005 | Peyman ..................... 424/94.64 |
| 7,524,826 B2 | * | 4/2009 | Austin et al. ................ 514/44 R |
| 2004/0146959 A1 | * | 7/2004 | Graham et al. .................. 435/15 |
| 2004/0235078 A1 | * | 11/2004 | Rosen et al. .................... 435/13 |

FOREIGN PATENT DOCUMENTS

| | | |
|---|---|---|
| EP | 0 420 332 | 4/1998 |
| WO | WO 03/093831 | 11/2003 |
| WO | WO 2006/036744 | 4/2006 |

OTHER PUBLICATIONS

Leytus et al. Biochemical J. (1983) 215(2): 253-260; abstract only downloaded from STN Jan. 30, 2011.*
Small et al. Quarterly J. Medicine, New Series (1987) 1025-1031.*
Tappenden et al. J. Thrombosis Haemostasis (Aug. 2005) vol. 3, Suppl. 1, abstract from the XXth Congress, Aug. 6-12, 2005 abstract No. P1897; downloaded from http://www.blackwellpublishing.com/isth2005/abstract.asp?id=47503; Jan. 30, 2011.*
Haughhland, R. Molecular Probes Handbook of Fluorescent Probes and Research Chemicals (1996) (Molecular Probes, Inc: Eugene OR), p. 227.*
Kosow, D. Biochemistry (1975) 14(20): 44594465.*
U.S. Appl. No. 60/612,580, filed Sep. 22, 2004 to Goldenberg et al.*
Gaffney et al. "A commentary of new methodologies in hemostasis using chromogenic substrates" Perspectives Hemostasis, Sel. Proc. Symp. 1st, 2nd (1981) Meeting date 1979-1980 pp. 405-417. Editor: J. Fareed (Pergamon Press: Mew York, NY).*
Pentapharm: Pefafluor uPA (Pefa-5243) Highly Sensitive Fluorogenic Peptide Substrate for Urokinase (uPA), http://www.pentapharm.com/graphics/Pentapharm/download/diagnostics/Fluorogenic_Substrates/Dse_Fluorogenic_Substrates.pdf> (retrieved Mar. 31, 2006).
KJ Dean et al., Simultaneous-Deterrnination of Phenytoin and Phenobarbital in Serum or Plasma by Substrate-Labeled Fluorescent Immunoassay, Clin. Chem, 29/6, 1051-1056 (1983).

* cited by examiner

*Primary Examiner* — Susan Hanley
(74) *Attorney, Agent, or Firm* — Vedder Price P.C.; Thomas J. Kowalski; Deborah L. Lu

(57) ABSTRACT

Provided is a hemostasis assay comprising a reaction mixture comprising a blood product to be tested, a trigger molecule for inducing thrombin generation, a thrombin-specific substrate which, upon cleavage by thrombin, produces a measurable thrombin-specific signal, a trigger molecule for inducing plasmin generation, a plasmin-specific substrate which, upon cleavage by plasmin, produces a measurable plasmin-specific signal, a phospholipid-containing surface, and calcium ions. The assay allows determination of the amount of thrombin and the amount of plasmin generated in the reaction mixture in time, starting at t=0, by measuring the thrombin-specific and plasmin-specific signals.

27 Claims, 12 Drawing Sheets

HEMOSTASIS ASSAY

CROSS-REFERENCE TO RELATED APPLICATIONS

This application is a continuation-in-part of International application no. PCT/EP2006/000184, filed Jan. 9, 2006, published as WO 2006/072602 on Jul. 13, 2006, and claiming priority to European application no. 05075030.6, filed Jan. 7, 2005.

The foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to an assay for simultaneously determining two or more reaction parameters, in particular thrombin generation and plasmin generation. The invention further provides a kit for performing the assay.

BACKGROUND

Upon normal physiological conditions, hemostasis, the readiness of the blood to clot to prevent blood loss, is kept in hemostatic balance by feedback mechanisms. The hemostatic balance is dependent on both the pro and anticoagulant pathway as well as the fibrinolytic system. In case the hemostatic balance is out of equilibrium, pathological clotting (vessel blockage) or bleeding (hemorrhage) can supplant normal hemostasis.

Abnormalities of the hemostatic system can be acquired or congenital. In such cases it is clinically essential to diagnose, monitor, and manage the patient in order to optimize therapeutic intervention.

Most coagulation testing involves end-point assays, which detect the clotting time of blood plasma or the real time clot lysis by means of turbidimetry. Although performed routinely, the currently available coagulation assays have inherent limitations that make them potentially unreliable as tools for monitoring increased coagulation. Moreover, there is not always a good correlation between the results of coagulation tests and the prevention of postoperative haemorrhage or recurrent thrombosis.

Most of the limitations relate to the fact that these are end-point tests that measure the time of clot formation in vitro and require the addition of exogenous reagents (such as $Ca^{2+}$ ions to replenish those bound by an anticoagulant), and thus do not necessarily reflect the patient's thrombotic potential (clotting potential).

As compared to the tests described above EP-420 332 discloses an improved thrombin generation assay. In this assay not only information is gathered about the clotting of plasma but also about the total thrombin generation after clot formation. These assays were first performed with chromogenic substrates and later on with fluorogenic substrates. Furthermore, several thrombin generation assays with platelet poor and platelet rich plasma are disclosed.

In these assays again the limitation is the measurement of increased coagulability (thrombophilia). Thrombophilia is a term used to describe a group of conditions in which there is an increased tendency, often repeated and often over an extended period of time, for excessive clotting.

A need therefore exists for a new assay that does not have the above indicated drawbacks, that is more simple and can measure the fibrinolysis in dependency of thrombin generation. It is the object of the invention to provide such assay.

SUMMARY OF THE INVENTION

In the research that led to the invention a new assay, in particular a fluorimetric assay, was developed in which thrombin generation as well as plasmin generation can be determined in time, simultaneously in one single well. The hemostasis assay of the invention differs from existing assays in two ways. The assay of the invention provides simultaneous detection of the generation of both thrombin and plasmin in one single well. Furthermore, the assay uses thrombin generation dependent plasmin generation instead of the addition of thrombin or fibrin. This leads to the possibility to measure abnormalities in coagulation induced by aberrations in fibrinolysis.

The invention thus relates to a hemostasis assay comprising the provision of a reaction mixture comprising a blood product to be tested, a trigger molecule for inducing thrombin generation, a thrombin-specific substrate that upon cleavage by thrombin produces a measurable thrombin-specific signal, a trigger molecule for inducing plasmin generation, a plasmin-specific substrate that upon cleavage by plasmin produces a measurable plasmin-specific signal, calcium ions and a phospholipid-containing surface, and determining the amount of thrombin and the amount of plasmin generated in the reaction mixture in time starting at t=0 by measuring the thrombin-specific and plasmin-specific signals.

The assay of the invention can suitably be performed in one single container. For bulk testing of blood samples the container in which the assay is performed is suitably a well of a microtitre plate. Such microtitre plates can be automatically processed in equipment that is well-known in the art. In one embodiment, the reagents are suitably contained in the container before the blood sample is added and can for example be coated to the wall or be present in lyophilized form. This is in particular useful in kits. However, the other way round, i.e. first adding the blood product to the well and then the other reagents is also possible.

The assay of the invention can be used for determining the thrombin and plasmin generation in various blood products, such as plasma, whole blood, drain liquid and platelet-rich plasma.

The phospholipid-containing surface consists for example of cephalin, cells, in particular endothelial cells, blood platelets, bacteria, viruses, matrices of endothelial cells or microvessels or other surfaces known to the person skilled in the art.

The trigger molecule for inducing generation of thrombin is suitably tissue factor (TF). TF mediates hemostasis by complexing with factor VIIa to directly convert X to Xa (extrinsic pathway), or indirectly by generating Xa by converting IX to IXa, which, in turn, complexes with VIIIa to convert X to Xa. Factor Xa, once generated, complexes with its co-factor, Va, to convert prothrombin (II) to thrombin (IIa). TF is preferred because it is the same trigger that is found in the body for the extrinsic pathway. Triggers for the intrinsic route are for example surfaces like glass, kaoline, or an acid.

Plasmin is formed by activation of the pro-enzyme, plasminogen, by plasminogen activators. Tissue plasminogen activators are found in most tissues. The trigger molecule for inducing generation of plasmin in the assay of the invention is suitably tissue plasminogen activator (tPA) because it is also the trigger in the natural situation in the body. tPA is activated by the thrombin formed in the reaction mixture. Examples of other triggers are urokinase and streptokinase.

The hemostasis assay of the invention uses preferably two fluorescent substrates, one for thrombin and one for plasmin, with different fluorescent excitation and emission spectra. After cleavage of the thrombin-specific fluorescent substrate by thrombin the fluorescent signal can be determined after excitation at the emission wavelength. The same holds true for the plasmin-specific fluorescent substrate.

Preferably two fluorescent substrates are chosen, that do not interfere with each other. In practice this means that the spectra of the different fluorescent substrates do not overlap. The assay of the invention can thus be performed to simultaneously measure both thrombin and plasmin generation. Both products can be determined in real time in one single well by using a fluorimeter equipped with two sets of filters. Examples of suitable substrates are the following: thrombin specific substrate coupled to 7-amino-4-methylcoumarin (AMC) (Bz-β-Ala-Gly-Arg-AMC-AcOH), and plasmin specific substrate coupled to rhodamine 110 (bis-(CBZ-L-phenylalanyl-L-arginine amide)).

The assay of the invention can be used to determine the effects of drugs, proteins, cells or other additives on both thrombin and plasmin generation and also the effect of a disturbed thrombin or plasmin generation on plasmin generation or thrombin generation, respectively. In order to measure the effect of such additives they can be added to the reaction mixture. These additives can also be coated to the wells in the container in which the assay is performed, such as the wells of 96-well plates. When endothelial cells are part of the reaction mixture they may be cultured in the wells.

Furthermore, different conditions can be chosen to start the reaction. For example, different concentrations of the reagents can be used.

The method of the invention has the following advantages compared to the currently available tests. Information about the extrinsic as well as intrinsic clotting pathways is obtained in one assay. To date this information can only be gathered by performing the APTT as well as the PT standard clotting assays. The invention further provides the possibility to determine also hypercoagulability, which is not possible with the standard thrombin generation assay performed in platelet poor plasma. With the assay of the invention straightforward analysis of thrombin generation without defibrination of plasma is possible. This pre-conditional step is required in the known thrombin generation assay of Hemker. Furthermore, the assay of the invention provides direct and on-line analysis of both thrombin and plasmin generation, which allows direct interpretation of the results. Moreover, immediate results are obtained about fibrinolysis and the effect of fibrinolysis on coagulation. No pre-conditional steps have to be performed to analyse fibrinolysis. These steps are a prerequisite in the euglobulin clot lysis test.

In addition to the specific assay described above, the invention provides a more general assay in which two or more reactions are simultaneously analysed. The main requirement is that the spectra of the different substrates that are processed in the reaction to be tested do not overlap.

Such general method comprises provision of a reaction mixture comprising a surface, a sample to be tested, trigger molecules for inducing the reactions to be measured, substrates that produce a measurable signal that is the result of the reaction, and determination of the signals generated in the reaction mixture in time starting at t=0. The surface is in particular a phospholipid surface for thrombin generation and intrinsically formed fibrin for plasmin generation.

In the specific embodiment of the invention the reactions to be tested are thrombin generation and plasmin generation. Other pairs of reactions can also be tested, either with different pairs of coagulation factors and/or cells. An example is thrombin generation and release of platelet specific enzymes. The substrate depends on the enzyme to be tested. In general the system can accept even more than two analyses in one experiment as long as the spectra do not overlap.

The invention further relates to a kit for performing the assay of the invention comprising a container comprising one or more of the following reagents: a trigger molecule for inducing thrombin generation, a thrombin-specific substrate that upon cleavage by thrombin produces a measurable thrombin-specific signal, a plasmin-specific substrate that upon cleavage by plasmin produces a measurable plasmin-specific signal, a trigger molecule for inducing plasmin generation, a surface and calcium ions. The other reagents of this list that are not present in the container are either part of the kit or can be added separately. It is important to have all reagents present upon performing the assay. The reaction is started when all reagents and the blood product to be tested are present in the reaction mixture.

The different embodiments of the various reagents have been described above.

BRIEF DESCRIPTION OF THE DRAWINGS

In the Examples that follow the assay of the invention has been tested using different patient samples. Both intra- and inter-assay variations were established. Reference is made to the following figures.

Figure 1:
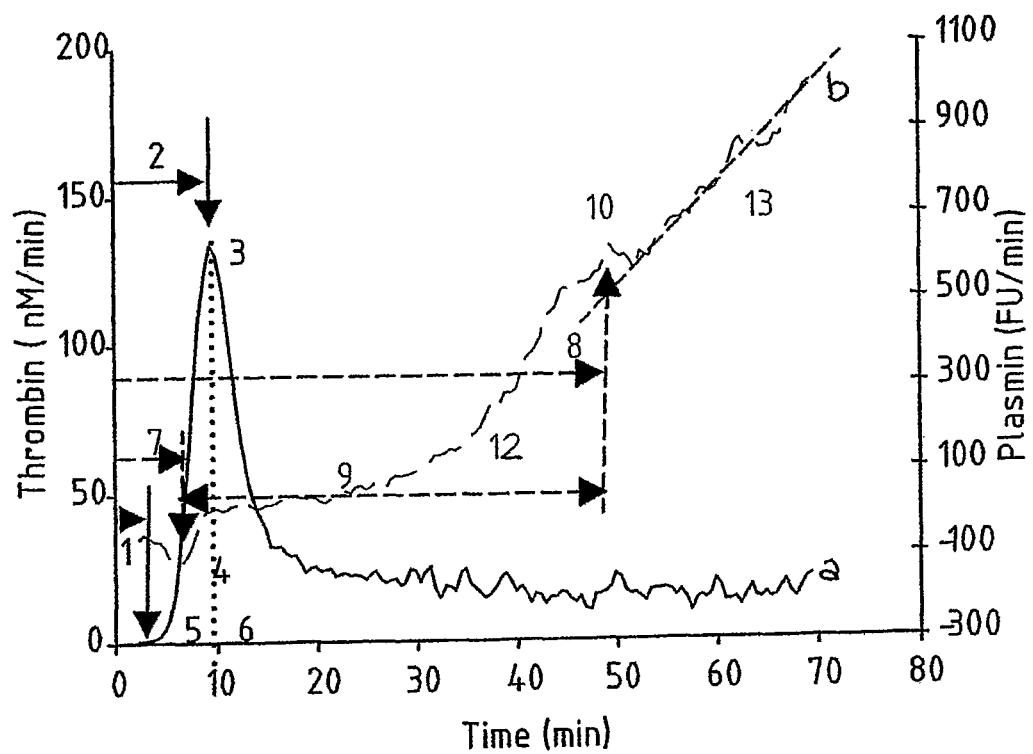
FIG. 1 shows a typical plot resulting from the assay of the invention. Line (a) represents the first derivative of thrombin generation expressed in nM/min (via a calculation curve). Line (b) represents the first derivative of plasmin generation expressed in FU/min. The following data can be generated out of the graph.

1: Thrombin generation lag time
2: Time to thrombin peak
3: Maximal thrombin generation
4: Thrombin potential
5: Procoagulant thrombin potential
6: Anticoagulant thrombin potential
7: Plasmin generation drop time (start clot formation)
8: Plasmin generation peak time (solubilized clot)
9: Clot lysis time
10: Plasmin generation level at plasmin generation peak time
12: Plasmin potential acceleration phase (clot lysis area)
13: Plasmin potential (measured over 10 minutes)

Figure 2A:
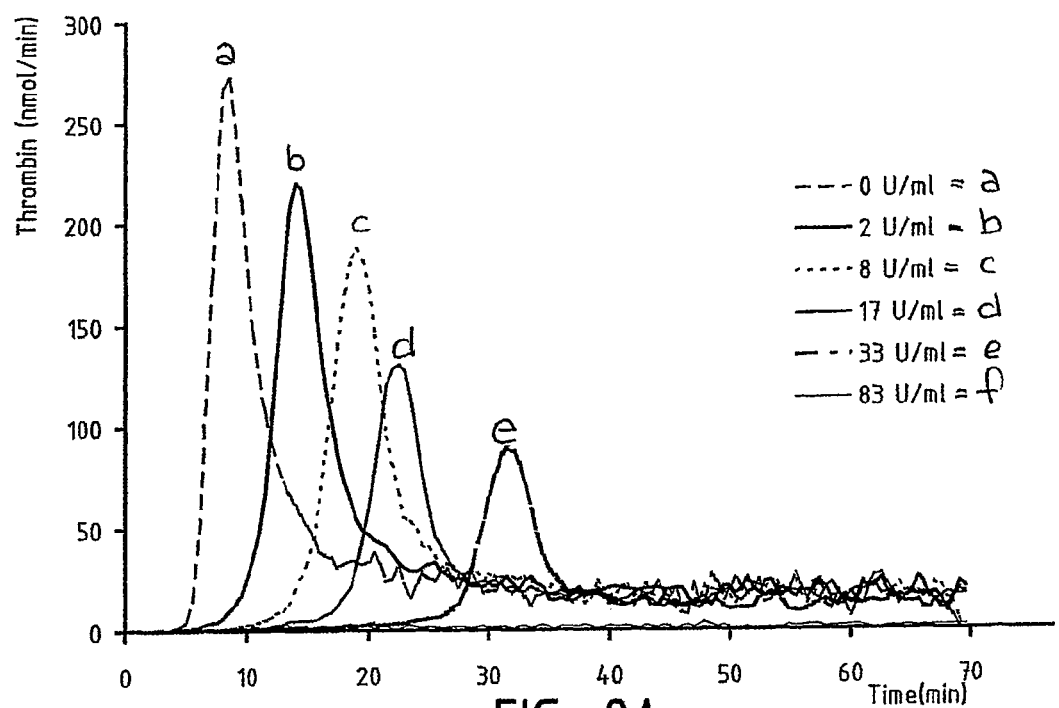
Figure 2B:
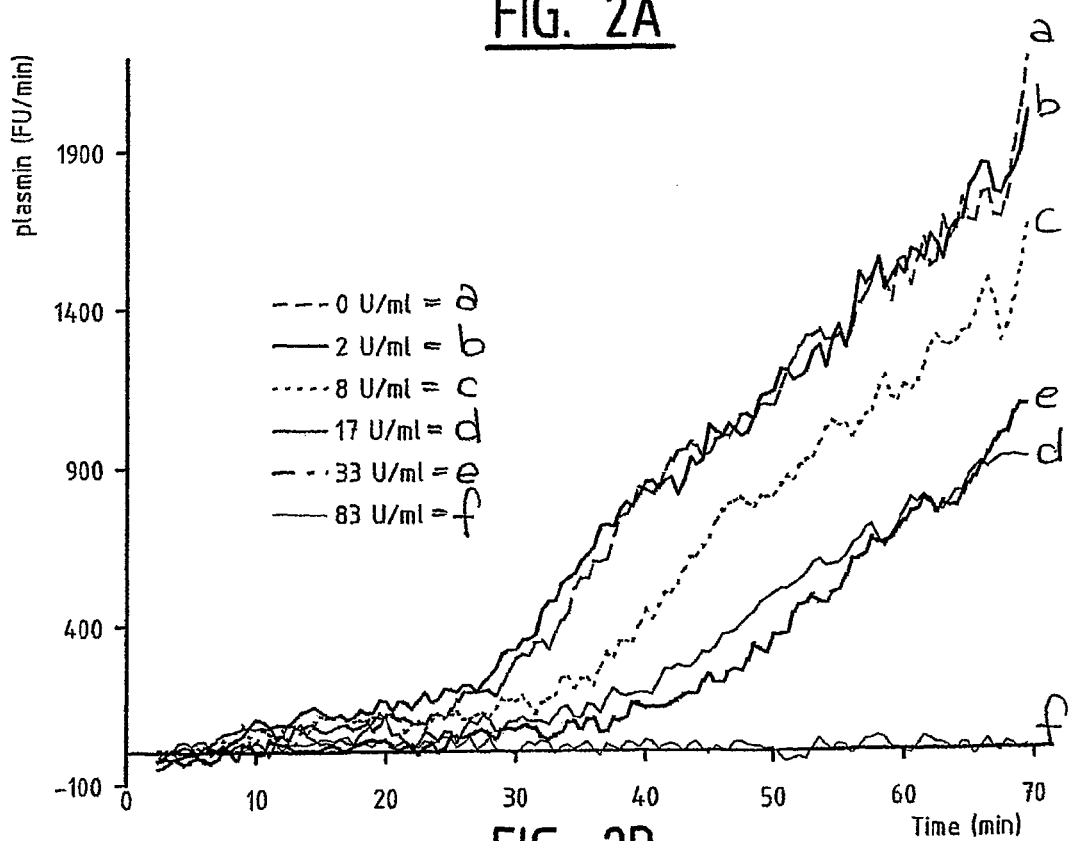

FIGS. 2A and 2B show thrombin (2A) and plasmin (2B) generation in the presence of different hirudin concentrations using normal pooled citrated plasma.

Figure 3A:
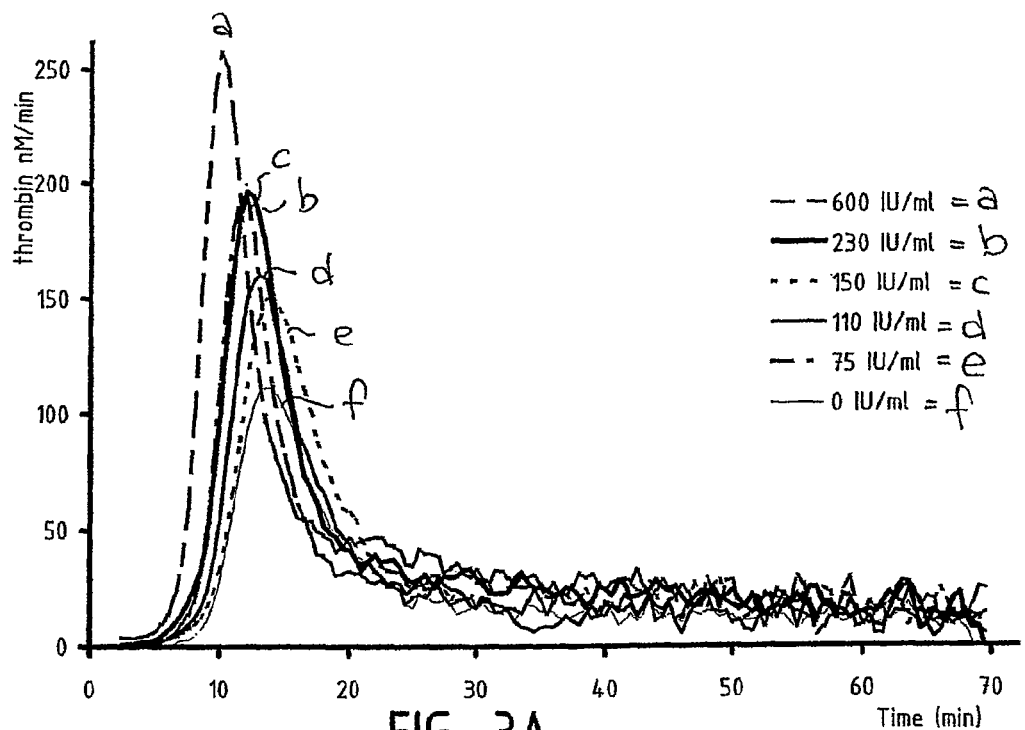
Figure 3B:
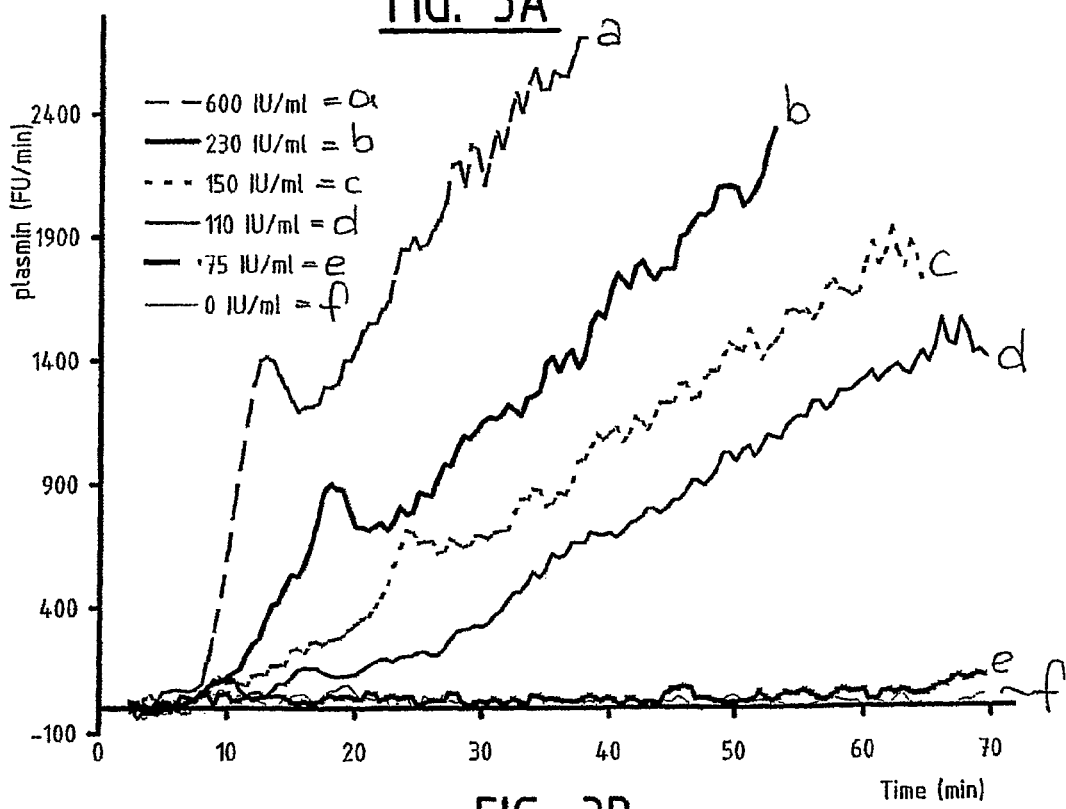

FIGS. 3A and 3B show the effect of tPA titration on thrombin (3A) and plasmin (3B) generation using normal pooled plasma.

Figure 4A:
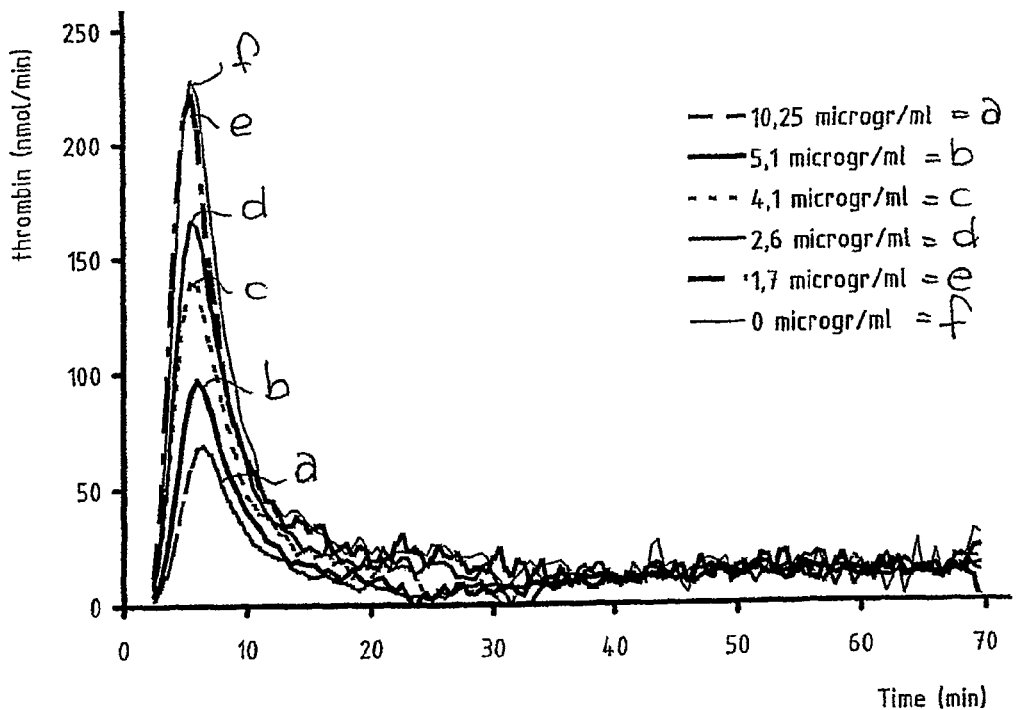
Figure 4B:
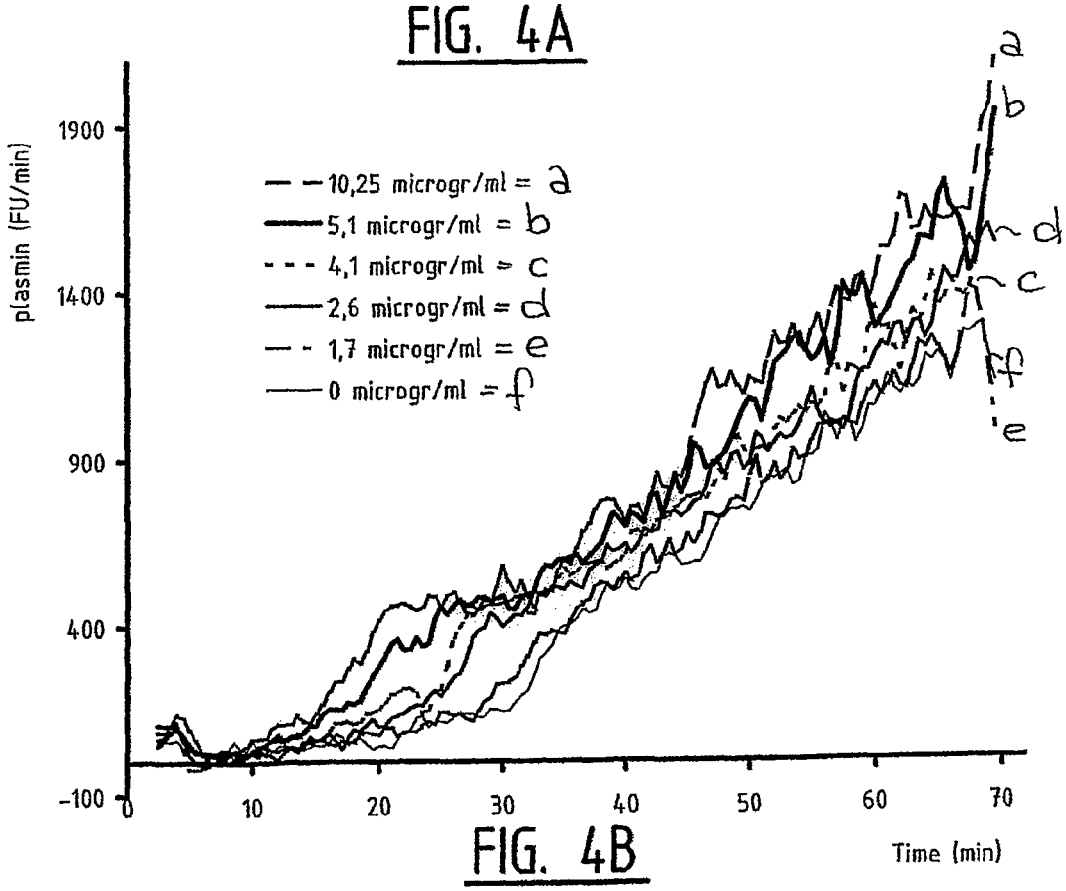

FIGS. 4A and 4B show thrombin (4A) and plasmin (4B) generation after the addition of active protein C using normal polled citrated plasma.

Figure 5A:
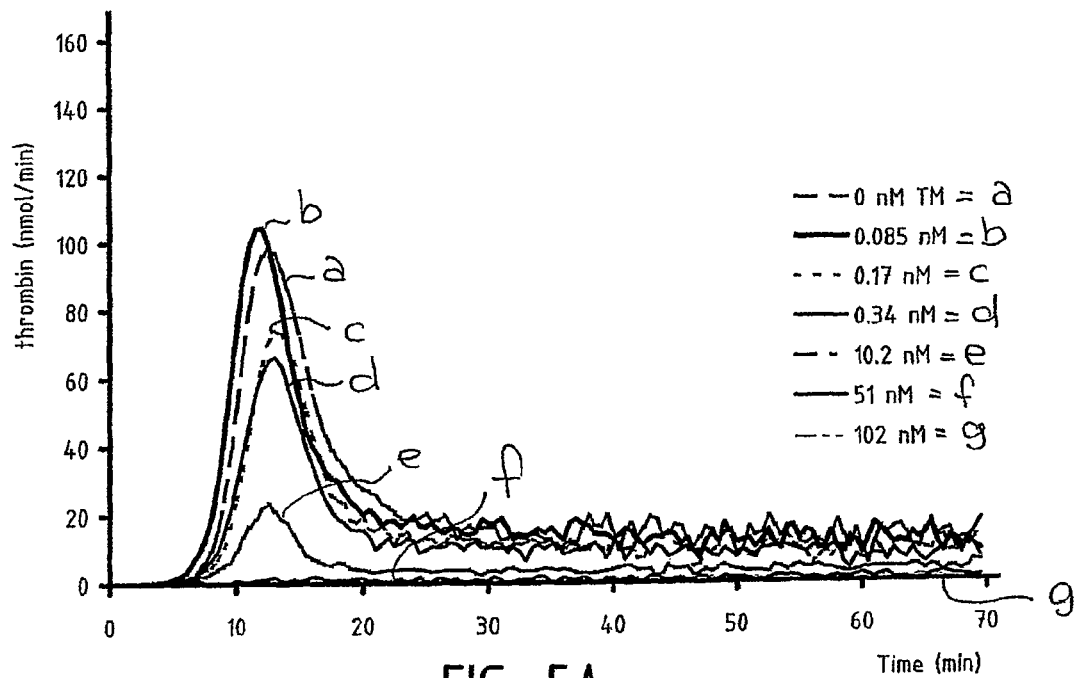
Figure 5B:
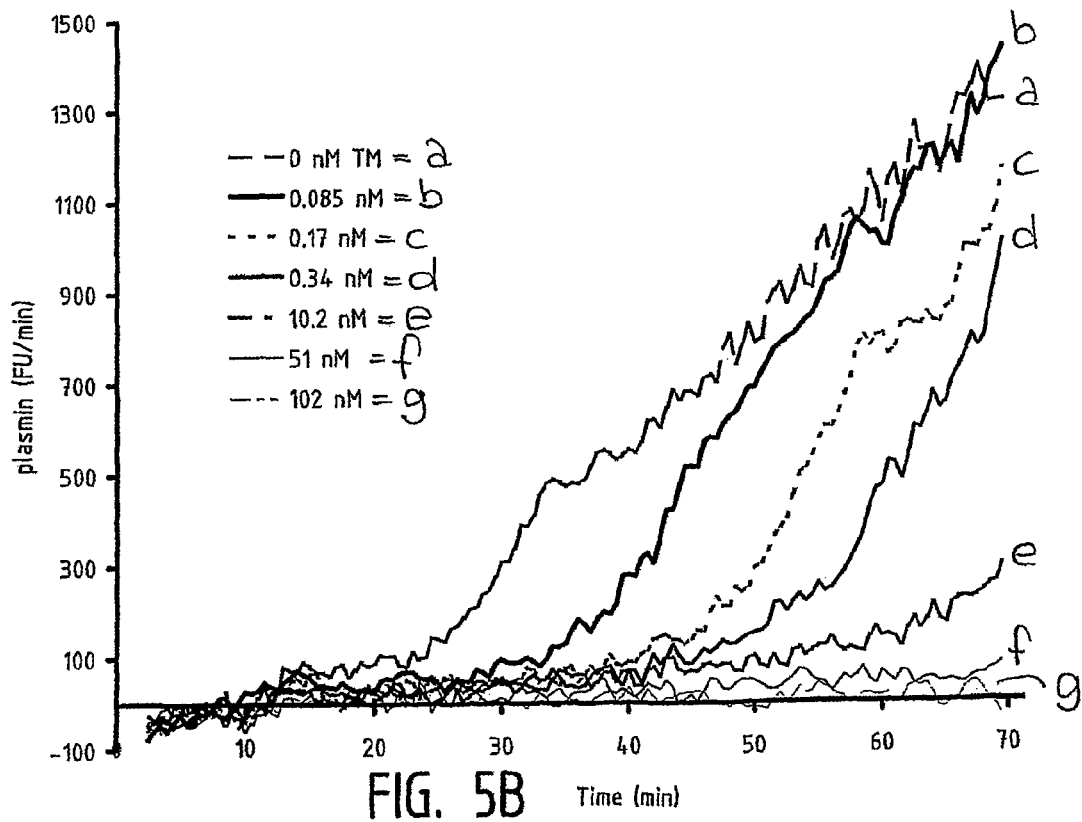

FIGS. 5A and 5B show thrombin (5A) and plasmin (5B) generation in the presence of different thrombomodulin (TM) concentrations using normal pooled citrated plasma.

Figure 6:
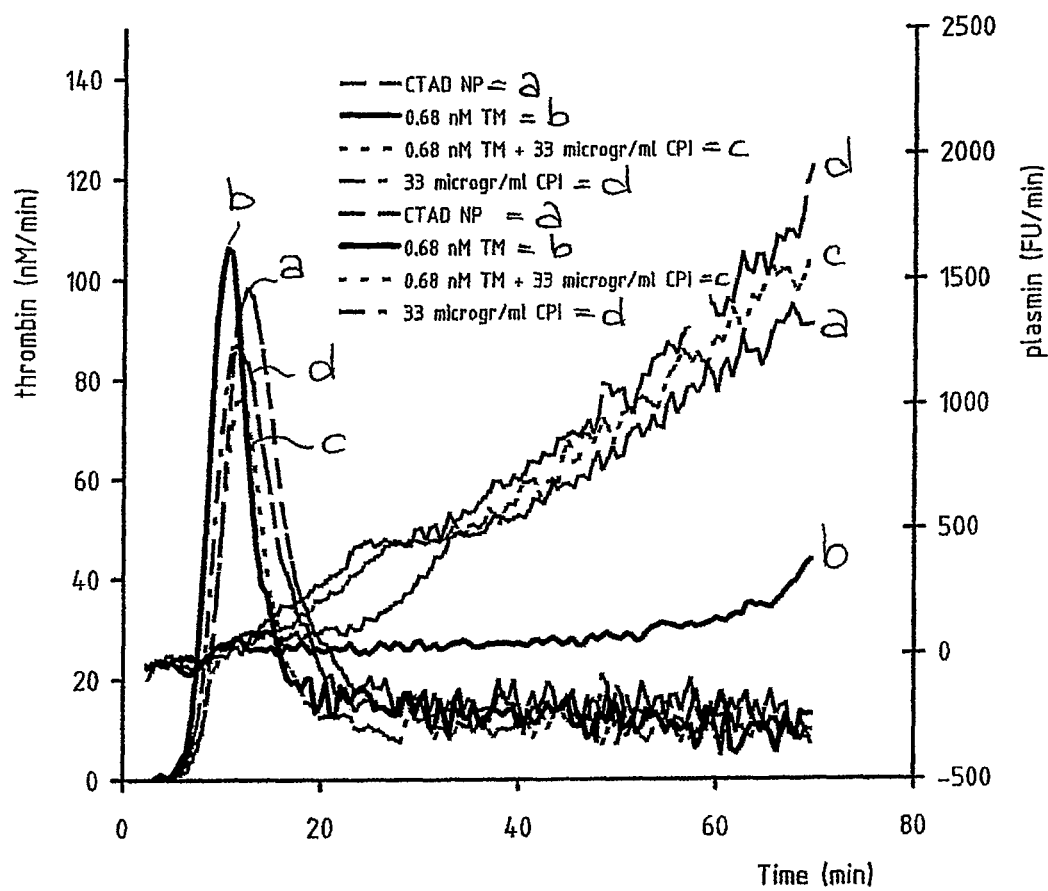

FIG. 6 shows thrombin generation and plasmin generation in the presence of thrombomodulin (TM) and carboxypeptidase inhibitor (CPI), the inhibitor of TAFI using normal pooled citrated plasma.

Figure 7A:
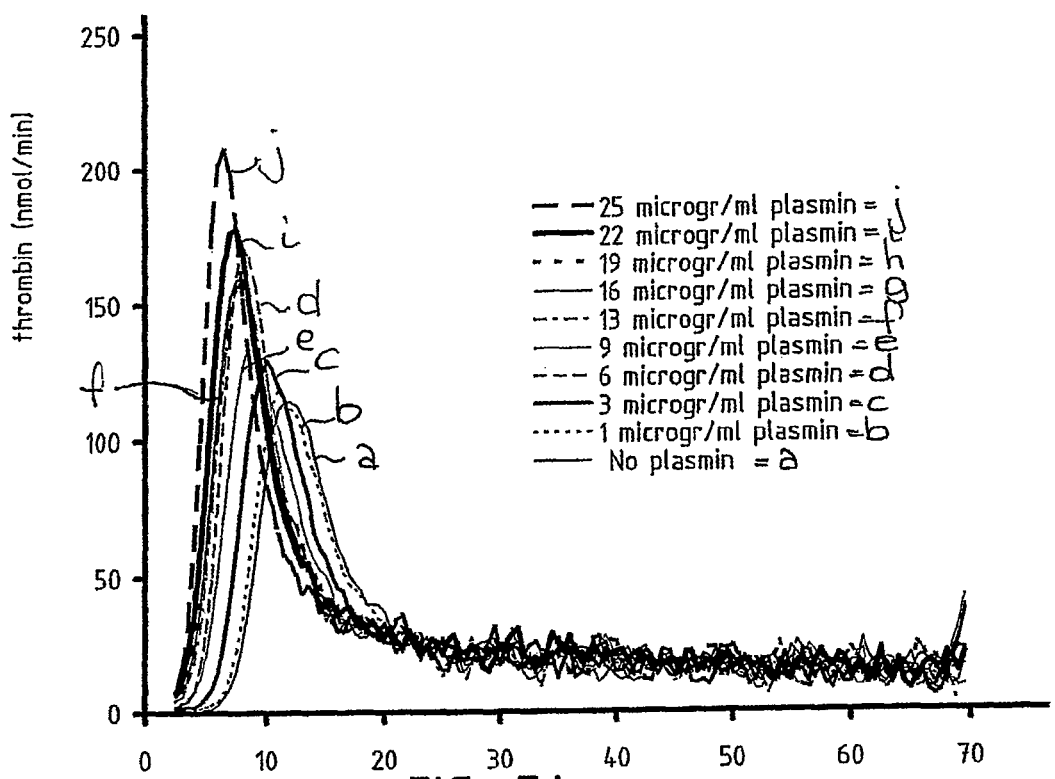
Figure 7B:
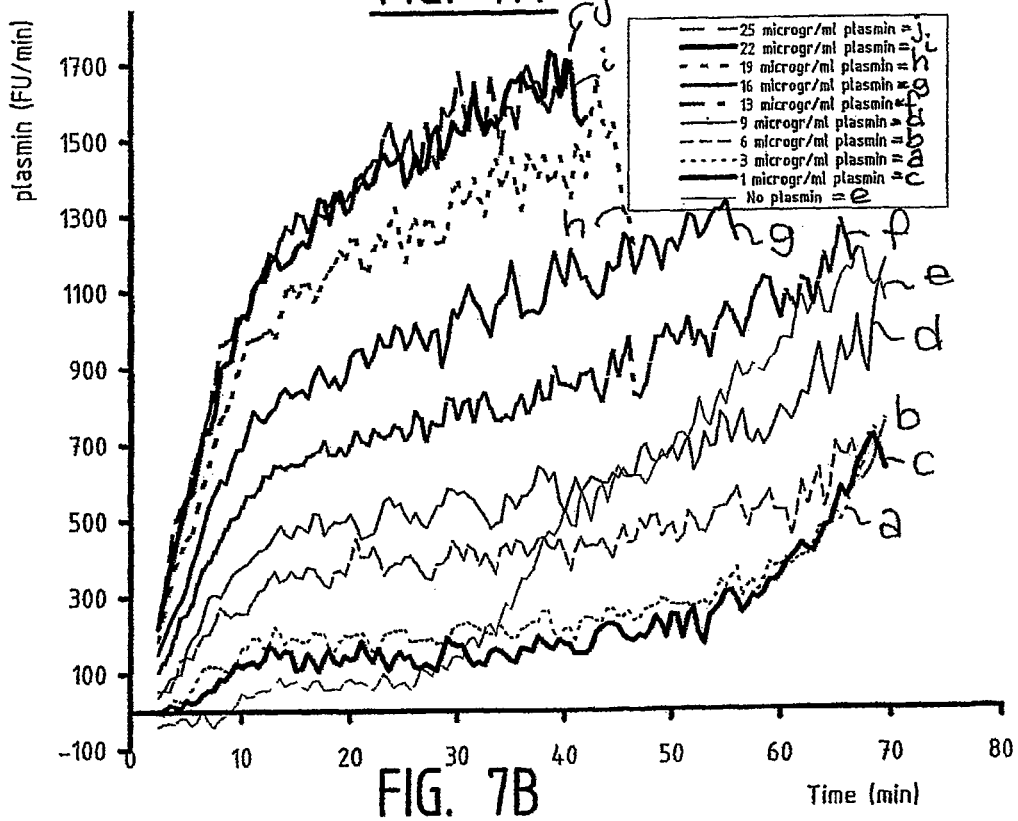

FIGS. 7A and 7B show thrombin (7A) and plasmin (7B) generation in the presence of different plasmin concentrations using normal pooled citrated plasma.

Figure 8:
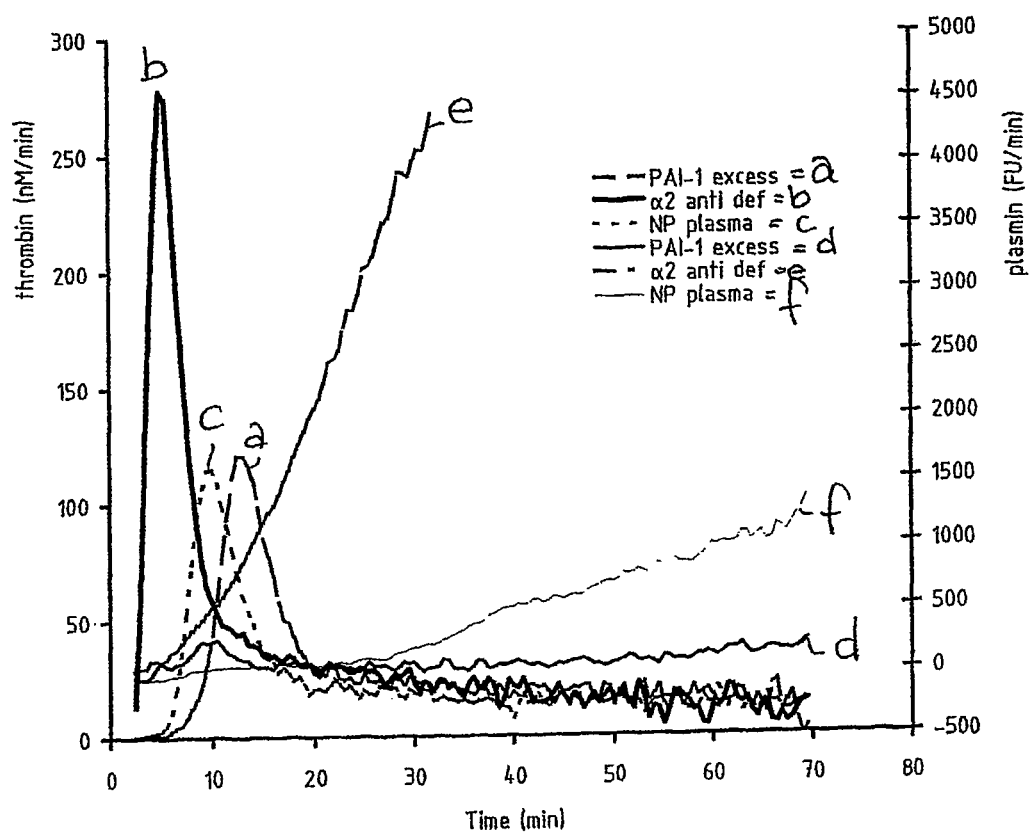

FIG. 8 shows thrombin and plasmin generation in normal pooled plasma of a patient with the alpha-2-anti-plasmin deficiency and a patient with a PAI-2 excess.

Figure 9:
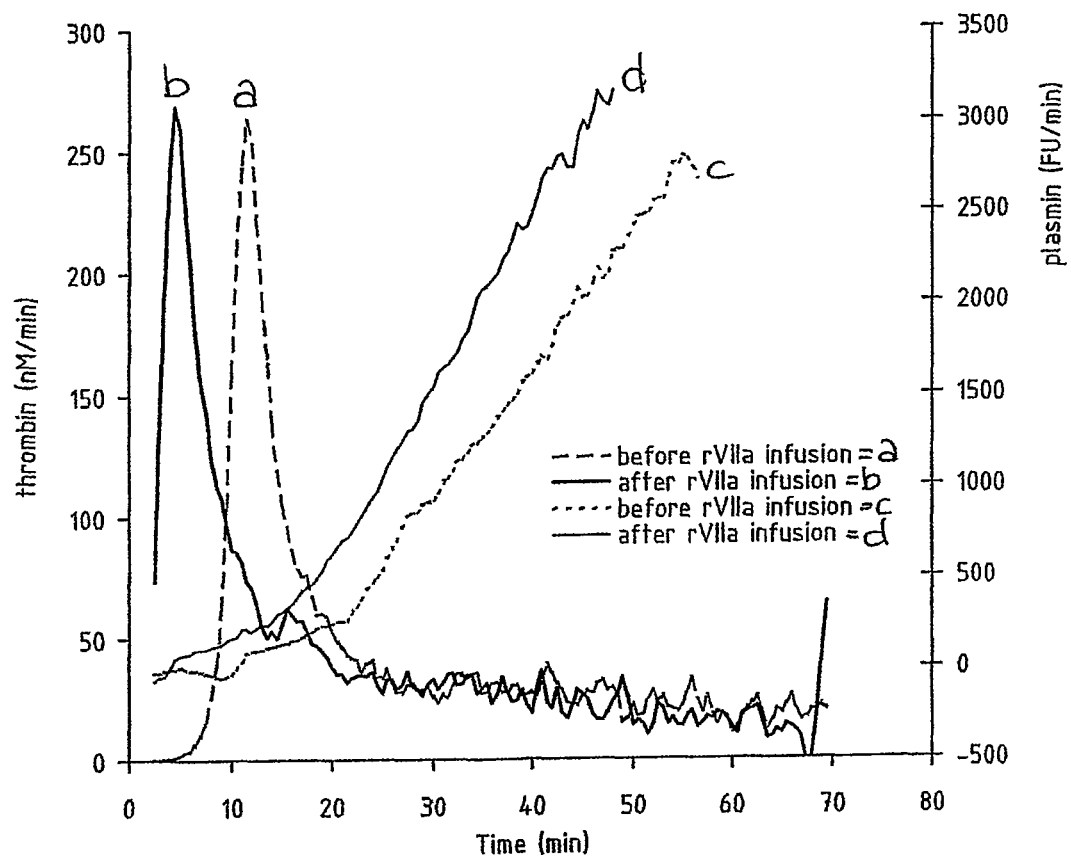

FIG. 9 shows thrombin and plasmin generation in plasma of a patient with Factor VII deficiency before and after Factor VIIa suppletion.

Figure 10:
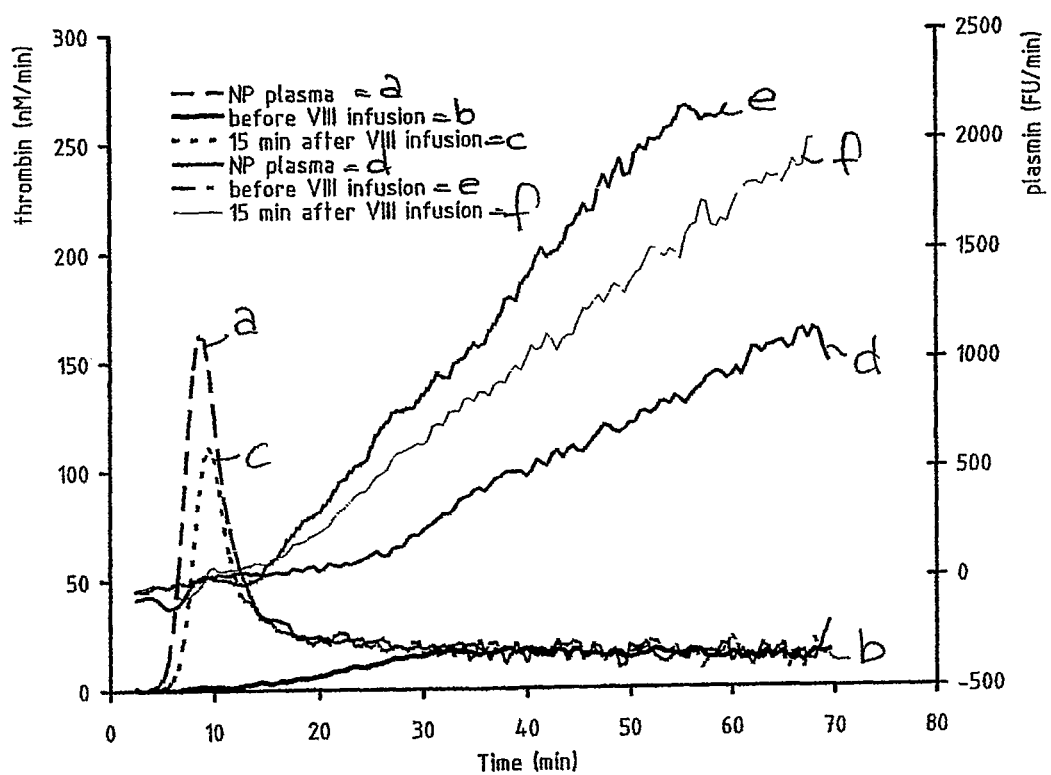

FIG. 10 shows thrombin (line a) and plasmin (line d) generation measured using a normal pooled citrated plasma. Lines b and c represent plasma of a severe Hemophilia A patient before factor VIII suppletion. Lines c and f represent plasma of a HA patient after factor VIII suppletion.

Figure 11:
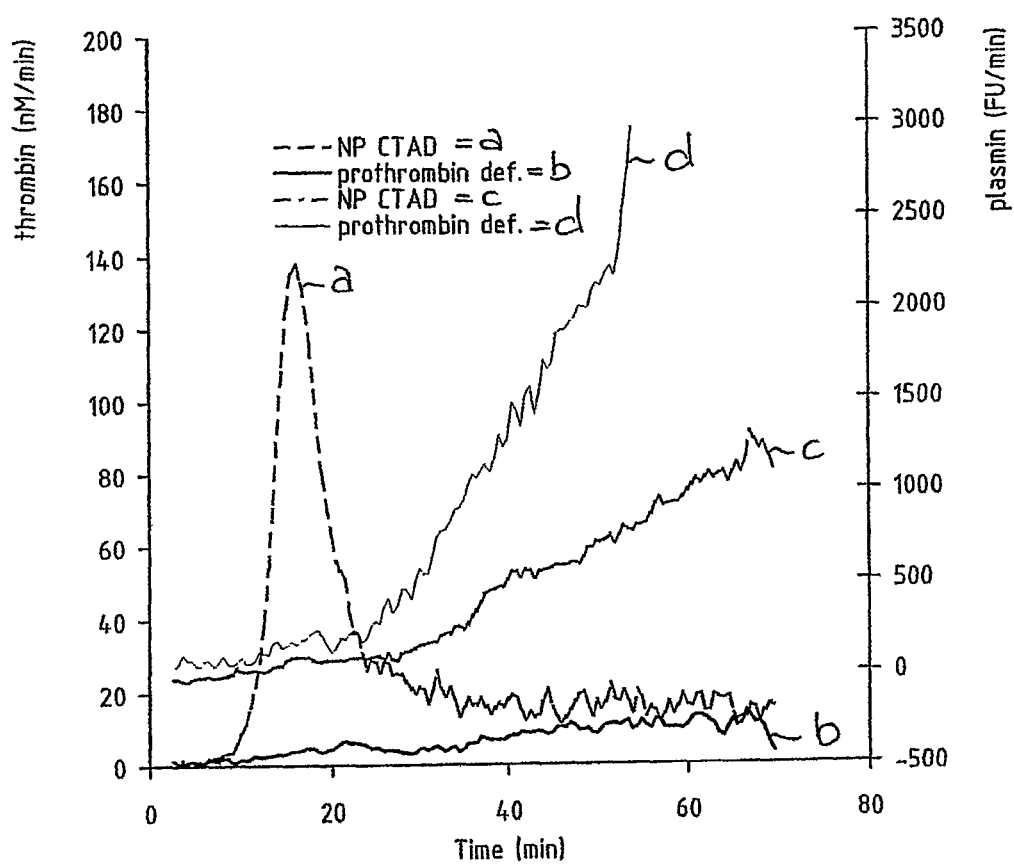

FIG. 11 shows thrombin (lines a and b) and plasmin (lines c and d) generation in normal pooled plasma (lines a and c) and plasma of a patient with a prothrombin deficiency (5%, lines b and d).

Figure 12:
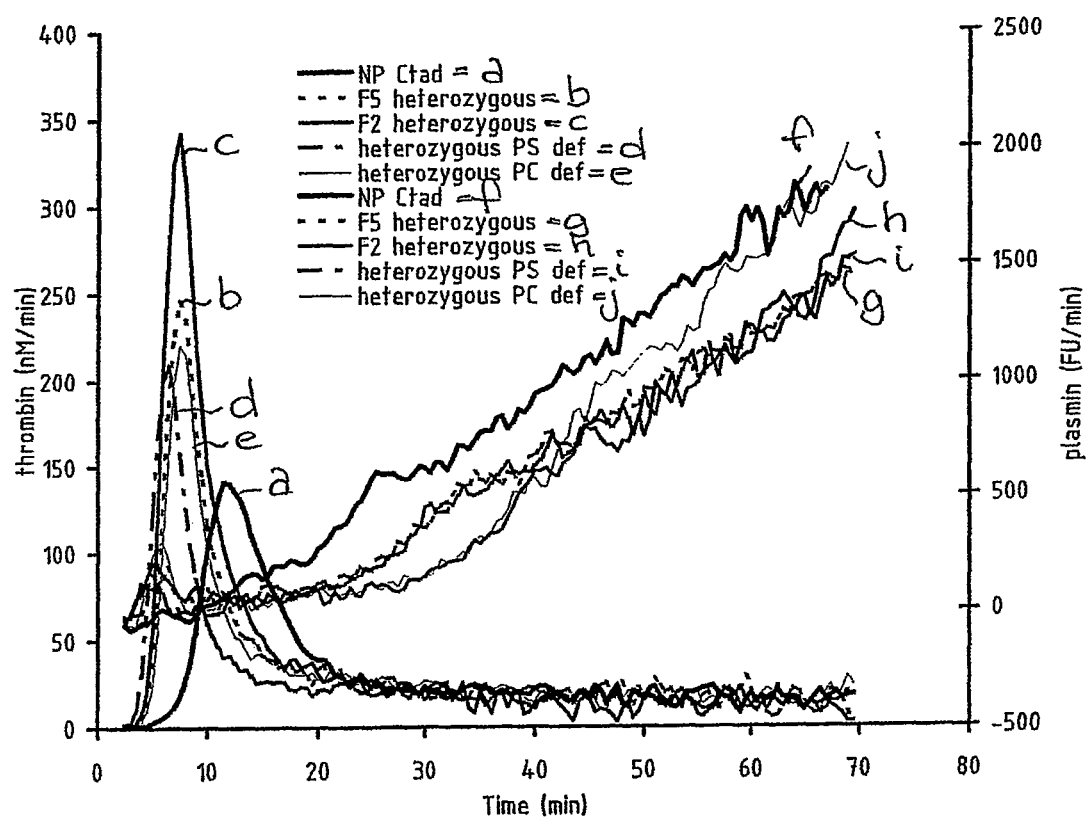

FIG. 12 shows Thrombin (lines a-e) and plasmin generation (lines f-j) in normal pooled plasma (lines a and f), and plasmas from a patient heterozygous for factor V Leiden (lines b and g), heterozygous for prothrombin mutation (lines c and h), protein S deficiency (lines d and i) and protein C deficiency (lines e and j).

EXAMPLES

Materials and Methods

1. Substrates

The substrates used for testing were the thrombin specific substrate coupled to 7-amino-4-methylcoumarin (AMC) (Pentapharm, Bz-β-Ala-Gly-Arg-AMC-AcOH, product number PF 082-21), and the plasmin specific substrate coupled to rhodamine 110 (Molecular Probes, rhodamine 110, bis-(CBZ-L-phenylalanyl-L-arginine amide), dihydrochloride. product number R-6502)

2. Assay Conditions

The assay conditions were:
80 µl citrated plasma
  2 µl cephalin (Roche product number 524298 (dissolved in 1 ml distilled water))
  2 µl recombinant Tissue Factor (Innovin, Dade Behring) (final concentration 0.1 pM)
  19 µl Tris buffered Saline (TBS, 50 mM Tris, 150 mM NaCl, pH 7.4) containing thrombin-specific fluorogenic substrate (final concentration 833 µM)
    plasmin fluorogenic substrate (final concentration 33 µM)
  17 µl TBS containing
    recombinant-tPA (Actilyse, Boehringer Ingelheim)(final concentration 150 IU/ml) $CaCl_2$ (final $Ca^{2+}$ concentration 16.7 mM)

3. Method

The fluorogenic signals were determined in a thermostated fluorimeter. For thrombin the excitation wavelength was 355 nm and the emission wavelength 460 nm. For plasmin the excitation wavelength was 485 nm and the emission wavelength 520 nm. The first derivatives were calculated and plotted. A typical plot is shown in FIG. 1.

4. Experiments

In Example 1 the above described experiment was performed with variations in the concentration of the various reagents. In Example 2 the plasma of various patient was tested.

Example 1

Effect of Different Reagents

1. Hirudin

The thrombin and plasmin generation in the presence of different hirudin concentrations was tested. The results are shown in FIG. 2 and Table 1.

TABLE 1

| | Hirudin | | | | | |
|---|---|---|---|---|---|---|
| | 0 U/ml | 2 U/ml | 8 U/ml | 17 U/ml | 33 U/ml | 83 U/ml |
| Lag Time Trombin Generation | 5.0 | 6.0 | 9.5 | 12.0 | 26.0 | N.D. |
| Time To Trombin Peak | 8.5 | 14.0 | 19.0 | 22.5 | 31.5 | N.D. |
| Trombin Peak Height | 273 | 220 | 187 | 130 | 89 | N.D. |
| Trombin Potential (ETP) | 2391 | 2233 | 1978 | 1425 | 933 | N.D. |
| ETP, procoagulant | 488 | 480 | 510 | 364 | 229 | N.D. |
| ETP, anticoagulant | 1903 | 1753 | 1469 | 1061 | 704 | N.D. |
| Plasmin Droptime | N.D. | N.D. | N.D. | N.D. | N.D. | N.D. |
| Plasmin Peaktime | N.D. | N.D. | N.D. | N.D. | N.D. | N.D. |
| Fibrin Lysis Time | N.D. | N.D. | N.D. | N.D. | N.D. | N.D. |
| Plasmin Peak Height | N.D. | N.D. | N.D. | N.D. | N.D. | N.D. |
| (PPeakHeight − PDropHeight)/FLT | N.D. | N.D. | N.D. | N.D. | N.D. | N.D. |
| Plasmin Potential, accel-Phase | N.D. | N.D. | N.D. | N.D. | N.D. | N.D. |
| Plasmin Potential, PPT + 10 min | N.D. | N.D. | N.D. | N.D. | N.D. | N.D. |

In FIG. 2, thrombin generation is presented in panel A whereas plasmin generation is shown in panel B. Different hirudin concentrations were used: 0 (line a), 2 (line b), 8 (line c), 17 (line d), 33 (line e) and 83 (line f)) U/ml.

Hirudin is a direct inhibitor of thrombin. Increasing the hirudin concentration both inhibits and retards thrombin generation, probably due to the fact that both factor V and Factor VIII are not activated by thrombin. In panel B it is shown that due to the inhibition of thrombin plasmin generation is only retarded as less fibrin is formed.

2. Trypsin Inhibitor

The addition of Corn Trypsin Inhibitor (CTI) the inhibitor of the intrinsic pathway was also tested. CTI does not affect both thrombin generation and plasmin generation indicating that the reaction is completely tissue factor dependent (data not shown).

3. tPA

For a tPA titration in normal pooled plasma different tissue-plasminogen activator (t-PA) concentrations were used as follows: 600 (line a), 230 (line b), 150 (line c, 110 (line d), 75 (line e) and 0 (line f) IU/ml. The results are shown in FIG. 3 and Table 2. Panel A of FIG. 3 represents thrombin generation. Panel B represents plasmin generation.

TABLE 2

| | t-PA titratibon | | | | | |
|---|---|---|---|---|---|---|
| | 600 IU/ml | 230 IU/ml | 150 IU/ml | 110 IU/ml | 75 IU/ml | 0 IU/ml |
| Lag Time Trombin Generation | 5.0 | 5.5 | 5.5 | 5.5 | 6.0 | 6.0 |
| Time To Trombin Peak | 10.0 | 12.0 | 14.0 | 13.0 | 11.5 | 13.5 |
| Trombin Peak Height | 257 | 196 | 151 | 160 | 195 | 111 |
| Trombin Potential (ETP) | 2095 | 2136 | 2024 | 1944 | 1945 | 1472 |
| ETP, procoagulant | 482 | 452 | 464 | 434 | 379 | 306 |
| ETP, anticoagulant | 1613 | 1684 | 1560 | 1510 | 1566 | 1166 |
| Plasmin Droptime | 5.0 | 5.5 | 7.0 | 5.5 | 6.0 | N.D. |
| Plasmin Peaktime | 13.0 | 18.0 | 24.0 | 38.5 | 45.0 | N.D. |
| Fibrin Lysis Time | 8.0 | 12.5 | 17.0 | 33.0 | 39.0 | N.D. |
| Plasmin Peak Height | 1418 | 901 | 716 | 703 | 74 | N.D. |
| (PPeakHeight − PDropHeight)/FLT | 169.7 | 71.0 | 43.0 | 21.4 | 1.4 | N.D. |
| Plasmin Potential, accel-phase | 4211 | 3808 | 4096 | 8052 | 1345 | N.D. |
| Plasmin Potential, PPT + 10 min | 12982 | 7721 | 6586 | 7469 | 391 | N.D. |

The higher the t-PA concentration the more plasmin and interestingly more thrombin is generated. Under normal conditions 150 IU/ml of t-PA (d) are used in the assay. Using this concentration allows the detection of thrombin-activatable fibrinolysis inhibitor (TAFI) activity. If the t-PA concentration is higher, the clot lysis is faster and supposable less TAFI activity can be observed.

4. Active Protein C

For testing thrombin (A) and plasmin (B) generation after the addition of active protein C, different APC concentrations were used as follows: 10.25 microgram/ml (line a), 5.1 (line b), 4.1 (line c), 2.6 (line d) 1.7 (line e), 0 (line f) microgram/ml. The results are shown in FIG. 4 and Table 3.

TABLE 3

| | APC | | | | | |
|---|---|---|---|---|---|---|
| | 10.25 microgr/ml | 5.1 microgr/ml | 4.1 microgr/ml | 2.6 microgr/ml | 1.7 microgr/ml | 0 microgr/ml |
| Lag Time Trombin Generation | 3.5 | 3.5 | 3.5 | 3.5 | 3.5 | 3.5 |
| Time To Trombin Peak | 6.5 | 6.0 | 5.5 | 5.5 | 5.5 | 5.5 |
| Trombin Peak Height | 69 | 97 | 140 | 166 | 222 | 229 |
| Trombin Potential (ETP) | 982 | 1176 | 1487 | 1682 | 1974 | 2109 |
| ETP, procoagulant | 138 | 163 | 202 | 233 | 345 | 326 |
| ETP, anticoagulant | 844 | 1014 | 1285 | 1449 | 1630 | 1783 |
| Plasmin Droptime | N.D. | N.D. | N.D. | N.D. | N.D. | N.D. |
| Plasmin Peaktime | N.D. | N.D. | N.D. | N.D. | N.D. | N.D. |
| Fibrin Lysis Time | N.D. | N.D. | N.D. | N.D. | N.D. | N.D. |
| Plasmin Peak Height | N.D. | N.D. | N.D. | N.D. | N.D. | N.D. |
| (PPeakHeight − PDropHeight)/FLT | N.D. | N.D. | N.D. | N.D. | N.D. | N.D. |
| Plasmin Potential, accel-phase | N.D. | N.D. | N.D. | N.D. | N.D. | N.D. |
| Plasmin Potential, PPT + 10 min | N.D. | N.D. | N.D. | N.D. | N.D. | N.D. |

In FIG. 4, the blue (f) represents the situation without APC addition. Active protein C inactivates factor Va and factor VIIIa. As such APC is part of the anticoagulant pathway. As expected addition of APC solely affects the thrombin potential (panel A) and affects TAFI activity as TAFI needs relatively large concentration of thrombin to be activated. In the situation without APC (dark blue) fibrinolysis is retarded.

5. Thrombomodulin

Thrombin and plasmin generation was measured in the presence of different Thrombomodulin (TM) concentrations. Thrombin generation is presented in panel A of FIG. 5 and Table 4 whereas plasmin generation is shown in panel B. Different concentrations of TM were used as follows: 0 (line a), 0.085 nM (line b), 0.17 (line c), 0.34 (line d), 10.2 (line c), 51 (line f) and 102 nM (line 9).

TM has two activities that are based on thrombin binding. First, TM activates Protein C to Active Protein C (APC). APC inactivates factor Va and Factor VIIIa and thus inhibits thrombin formation (A). The second activity is activation of the thrombin activatable fibrinolysis inhibitor (TAFI). TAFI inhibits fibrinolysis by removing carboxy terminal amino acids from fibrin and thereby removes the plasminogen binding site. The more TM the longer it takes to start plasmin generation which is expected to be an activity of TAFI (panel B). Activation of TAFI occurs at lower TM concentrations than activation of APC.

TABLE 4

|  | Thrombomodulin | | | | | | |
| --- | --- | --- | --- | --- | --- | --- | --- |
|  | 0 nM TM | 0.085 nM | 0.17 nM | 0.34 nM | 10.2 nM | 51 nM | 102 nM |
| Lag Time Trombin Generation | 5.0 | 4.5 | 6.0 | 5.5 | 4.5 | N.D. | N.D. |
| Time To Trombin Peak | 12.5 | 12.0 | 13.0 | 13.0 | 12.5 | N.D. | N.D. |
| Trombin Peak Height | 98 | 104 | 74 | 66 | 23 | N.D. | N.D. |
| Trombin Potential (ETP) | 1419 | 1392 | 1023 | 916 | 318 | N.D. | N.D. |
| ETP, procoagulant | 267 | 299 | 189 | 196 | 60 | N.D. | N.D. |
| ETP, anticoagulant | 1152 | 1093 | 834 | 720 | 258 | N.D. | N.D. |
| Plasmin Droptime | N.D. | N.D. | N.D. | N.D. | N.D. | N.D. | N.D. |
| Plasmin Peaktime | N.D. | N.D. | N.D. | N.D. | N.D. | N.D. | N.D. |
| Fibrin Lysis Time | N.D. | N.D. | N.D. | N.D. | N.D. | N.D. | N.D. |
| Plasmin Peak Height | N.D. | N.D. | N.D. | N.D. | N.D. | N.D. | N.D. |
| (PPeakHeight − PDropHeight)/FLT | N.D. | N.D. | N.D. | N.D. | N.D. | N.D. | N.D. |
| Plasmin Potential, accel-phase | N.D. | N.D. | N.D. | N.D. | N.D. | N.D. | N.D. |
| Plasmin Potential, PPT + 10 min | N.D. | N.D. | N.D. | N.D. | N.D. | N.D. | N.D. |

6. Carboxypeptidase Inhibitor

Thrombin generation and plasmin generation were measured in the presence of thrombomodulin (TM) and carboxy peptidase inhibitor (CPI), the inhibitor of TAFI. Line (a) represent the normal situation without any addition. Line (b) represents the situation in the presence of 0.68 nM TM. Line (d) represent the situation with 33 microgram/ml CPI and line (c) the situation with TM and CPI. FIG. 6 and Table 5 show the results.

Again, TM activates TAFI resulting in a retarded plasmin generation. In the presence of CPI, plasmin generation starts immediately. CPI also abolishes the effect of TM indicating that indeed TM activates TAFI. Thus, even in a normal situation there is TAFI activity.

TABLE 5

| | FIG. 6 | | | |
| --- | --- | --- | --- | --- |
| | CT ADNP | 0.68 nM TM | 0.68 nM + 33 microgr/ml CP | 33 microgr/ml CPI |
| Lag Time Trombin Generation | 5.0 | 5.5 | 5.0 | 4.5 |
| Time To Trombin Peak | 12.5 | 10.5 | 12.0 | 11.5 |
| Trombin Peak Height | 98 | 106 | 76 | 87 |
| Trombin Potential (ETP) | 1419 | 1260 | 1029 | 1369 |
| ETP, procoagulant | 267 | 228 | 205 | 227 |
| ETP, anticoagulant | 1152 | 1032 | 825 | 1143 |
| Plasmin Droptime | 9.0 | N.D. | 5.0 | 7.5 |
| Plasmin Peaktime | 37.5 | N.D. | 29.5 | 26.5 |
| Fibrin Lysis Time | 28.5 | N.D. | 24.5 | 19.0 |
| Plasmin Peak Height | 54.5 | N.D. | 457 | 459 |
| (P Peak Height − P Drop Height)/FLT | 19.7 | N.D. | 19.6 | 26.5 |
| Plasmin Potential, accel-phase | 5434 | N.D. | 4210 | 3960 |
| Plasmin Potential, PPT + 10 min | 5842 | N.D. | 4750 | 4749 |

7. Plasmin

Thrombin and plasmin generation were measured in the presence of different plasmin concentrations. Thrombin generation is presented in panel A of FIG. 7, whereas plasmin generation is shown in panel B (see also Table 6). The following final plasmin concentrations were used: by 0 (line a), 1 (line b), 3 (line c), 6 (line d), 9 (line e), 13 (line f), 16 (line g), 19 (line h), 22 (line i), 25 (line j) microgram/ml.

To prove that plasmin affects thrombin generation plasmin was directly added to the reaction mixture. As expected, addition of plasmin directly had an effect on the plasmin generation curve. Moreover, plasmin affects also thrombin generation as it shortens the lag-time of thrombin generation and increases the thrombin potential.

TABLE 6

| | series 1-10 | | | | | | | | | |
| --- | --- | --- | --- | --- | --- | --- | --- | --- | --- | --- |
| | 25 microgr/ml plasim | 22 microgr/ml plasim | 19 microgr/ml plasim | 16 microgr/ml plasim | 13 microgr/ml plasim | 9 microgr/ml plasim | 6 microgr/ml plasim | 3 microgr/ml plasim | 1 microgr/ml plasim | No plasmin |
| Lag Time Trombin Generation | 3.5 | 3.5 | 3.5 | 3.5 | 3.5 | 3.5 | 4.0 | 5.0 | 5.0 | 5.0 |
| Time To Trombin Peak | 6.5 | 7.5 | 8.0 | 8.0 | 8.0 | 8.5 | 8.0 | 10.0 | 11.0 | 11.5 |
| Trombin Peak Height | 208 | 178 | 159 | 160 | 158 | 136 | 172 | 130 | 118 | 114 |
| Trombin Potential (ETP) | 1855 | 1739 | 1717 | 1927 | 2063 | 1960 | 2051 | 1839 | 1741 | 1729 |
| ETP, procoagulant | 403 | 439 | 418 | 428 | 398 | 307 | 340 | 324 | 290 | 296 |
| ETP, anticoagulant | 1452 | 1300 | 1299 | 1499 | 1666 | 1654 | 1711 | 1515 | 1451 | 1433 |
| Plasmin Droptime | N.D. | N.D. | N.D. | N.D. | N.D. | N.D. | N.D. | N.D. | N.D. | N.D. |
| Plasmin Peaktime | N.D. | N.D. | N.D. | N.D. | N.D. | N.D. | N.D. | N.D. | N.D. | N.D. |
| Fibrin Lysis Time | N.D. | N.D. | N.D. | N.D. | N.D. | N.D. | N.D. | N.D. | N.D. | N.D. |
| Plasmin Peak Height | N.D. | N.D. | N.D. | N.D. | N.D. | N.D. | N.D. | N.D. | N.D. | N.D. |

TABLE 6-continued

| | series 1-10 | | | | | | | | | |
|---|---|---|---|---|---|---|---|---|---|---|
| | 25 microgr/ ml plasim | 22 microgr/ ml plasim | 19 microgr/ ml plasim | 16 microgr/ ml plasim | 13 microgr/ ml plasim | 9 microgr/ ml plasim | 6 microgr/ ml plasim | 3 microgr/ ml plasim | 1 microgr/ ml plasim | No plasmin |
| (PPeakHeight − PDropHeight)/FLT | N.D. | N.D. | N.D. | N.D. | N.D. | N.D. | N.D. | N.D. | N.D. | N.D. |
| Plasmin Potential, accel-phase | N.D. | N.D. | N.D. | N.D. | N.D. | N.D. | N.D. | N.D. | N.D. | N.D. |
| Plasmin Potential, PPT + 10 min | N.D. | N.D. | N.D. | N.D. | N.D. | N.D. | N.D. | N.D. | N.D. | N.D. |

Example 2

Testing of Various Clinical Conditions

1. Fibrinolysis Patients

FIG. 8 shows the thrombin (line a-c) and plasmin (lines d-f) generation in normal pooled plasma (lines c, f) plasma of a patient with the alpha-2-anti-plasmin deficiency (lines b, e) and a patient with a PAI-2 excess (lines a, d) (see also Table 7).

TABLE 7

| | >200, series 1-3 | | |
|---|---|---|---|
| | PAI-1 excess | α2 antidef | NP plasma |
| Lag Time Trombin Generation | 6.0 | 3.5 | 4.5 |
| Time To Trombin Peak | 13.0 | 5.0 | 10.0 |
| Trombin Peak Height | 121 | 277 | 115 |
| Trombin Potential (ETP) | 1652 | 1786 | 1553 |
| ETP, procoagulant | 337 | 313 | 288 |
| ETP, anticoagulant | 1316 | 1473 | 1266 |
| Plasmin Droptime | N.D. | N.D. | N.D. |
| Plasmin Peaktime | N.D. | N.D. | N.D. |
| Fibrin Lysis Time | N.D. | N.D. | N.D. |
| Plasmin Peak Height | N.D. | N.D. | N.D. |
| (P Peak Height − P Drop Height)/FLT | N.D. | N.D. | N.D. |
| Plasmin Potential, accel-phase | N.D. | N.D. | N.D. |
| Plasmin Potential, PPT + 10 min | N.D. | N.D. | N.D. |

In this example it was observed that the patient with alpha2-AP (lines b, e) had a very increased plasmin generation and due to this a decreased lag-time in thrombin generation and even increased thrombin generation. The patient with a plasminogen-activator inhibitor type 2 (PAI-2) (lines a, d) excess shows an opposite effect. Plasmin generation is nearly absent and thrombin generation delayed. No effect on the total thrombin generation is observed.

2. Factor VII Deficiency

Thrombin and plasmin generation was measured in plasma of a patient with Factor VII deficiency before (lines a, c) and after Factor VIIa suppletion (lines b, d). The line a in FIG. 9 represents the thrombin and line c plasmin generation before factor VII(a) suppletion whereas the dashed lines b and d after 10 min of 40 microgram/ml factor VIIa suppletion. See also Table 8.

TABLE 8

| | series 1-2 | |
|---|---|---|
| | before rVIIa infusion | after rVIIa infusion |
| Lag Time Trombin Generation | 5.5 | 3.5 |
| Time To Trombin Peak | 11.5 | 4.5 |
| Trombin Peak Height | 263 | 269 |
| Trombin Potential (ETP) | 2547 | 2519 |
| ETP, procoagulant | 506 | 238 |
| ETP, anticoagulant | 2041 | 2281 |
| Plasmin Droptime | 9.0 | 3.5 |
| Plasmin Peaktime | 32.0 | 29.0 |
| Fibrin Lysis Time | 23.0 | 25.5 |
| Plasmin Peak Height | 1081 | 1458 |
| (P Peak Height − P Drop Height)/FLT | 49.3 | 58.8 |
| Plasmin Potential, accel-phase | 9039 | 12989 |
| Plasmin Potential, PPT + 10 min | 13257 | 18139 |

The patient has <1% factor VII activity and shows a delayed thrombin generation curve and a delayed plasmin generation curves (lines a and c). Suppletion of factor VIIa decreases the lag-time of thrombin and plasmin generation (lines b and d). Interestingly, no effect is observed in the total thrombin generation (thrombin potential) indicating that the Bouma loop is not disturbed (which is the case in patients with severe hemophilia A (HA)).

Like the thrombin generation, after activation plasmin generation is delayed equally fast. This might be explained by the fact that plasmin generation is triggered after fibrin formation. TAFI the inhibitor of fibrinolysis is equally activated.

3. Haemophilia A

The plasma of a patient with severe Hemophilia A was tested in the assay of the invention. FIG. 10 and Table 9 show the results.

TABLE 9

| | "28-12-2004, series 1-3" | | |
|---|---|---|---|
| | NP plasma | before VIII infusion | 15 min after VIII infusion |
| Lag Time Trombin Generation | 4.5 | N.D. | 5.5 |
| Time To Trombin Peak | 8.5 | N.D. | 9.5 |
| Trombin Peak Height | 162 | N.D. | 111 |
| Trombin Potential (ETP) | 1756 | N.D. | 1483 |
| ETP, procoagulant | 266 | N.D. | 199 |
| ETP, anticoagulant | 1490 | N.D. | 1284 |
| Plasmin Droptime | 6.0 | N.D. | 7.5 |
| Plasmin Peaktime | 41.0 | N.D. | 28.0 |
| Fibrin Lysis Time | 35.0 | N.D. | 20.5 |
| Plasmin Peak Height | 543 | N.D. | 585 |

TABLE 9-continued

| | "28-12-2004, series 1-3" | | |
|---|---|---|---|
| | NP plasma | before VIII infusion | 15 min after VIII infusion |
| (P Peak Height – P Drop Height)/FLT | 19.1 | N.D. | 32.2 |
| Plasmin Potential, accel-phase | 5743 | N.D. | 4232 |
| Plasmin Potential, PPT + 10 min | 5870 | N.D. | 7076 |

In FIG. 10, the straight lines represents the thrombin (lines a-c) and plasmin (lines d-f) generation measured using a normal pooled citrated plasma. The lines b and e represent plasma of a severe Hemophilia A patient before factor VIII suppletion whereas the lines c and f represents plasma of a HA patient after factor VIII suppletion.

It can be seen that thrombin generation is clearly diminished in the Hemophilia A patient and partly restored by factor VIII suppletion. Next, plasmin generation is enhanced in the patient before suppletion and partly restored after factor VIII suppletion. The explanation might be that TAFI the inhibitor of fibrinolysis is not activated (due to the low thrombin level) and thus more plasmin will be generated.

4. Prothrombin Deficiency

The assay of the invention was used to measure thrombin (line a and b, in FIG. 11) and plasmin (lines c and d) generation in normal pooled plasma (a and c) and plasma of a patient with a prothrombin deficiency (5%) (b and d). See also Table 10.

TABLE 10

| | new, series 1-2 | |
|---|---|---|
| | NP CTAD | prothrombin def |
| Lag Time Trombin Generation | 6.5 | N.D. |
| Time To Trombin Peak | 16.0 | N.D. |
| Trombin Peak Height | 137 | N.D. |
| Trombin Potential (ETP) | 1750 | N.D. |
| ETP, procoagulant | 402 | N.D. |
| ETP, anticoagulant | 1348 | N.D. |
| Plasmin Droptime | 13.0 | N.D. |
| Plasmin Peaktime | 42.0 | N.D. |
| Fibrin Lysis Time | 29.0 | N.D. |
| N.D.Plasmin Peak Height | 567 | N.D. |
| (P Peak Height – P Drop Height)/FLT | 18.9 | N.D. |
| Plasmin Potential, accel-phase | 5523 | N.D. |
| Plasmin Potential, PPT + 10 min | 5884 | N.D. |

The patient has a disturbed thrombin generation and as a consequence an increased fibrinolytic activity which might be explained partly by a lack of TAFI activation by thrombin. TAFI normally inhibits plasmin generation.

5. Thrombophilia Patients

Thrombin (lines a to e) and plasmin (lines f to j) generation was measured in normal pooled plasma (lines a and f), and in plasmas from various thrombophilia patients, namely a patient heterozygous for factor V Leiden (lines b and g), heterozygous for a prothrombin mutation (lines c and h), a patient having a protein S deficiency (lines d and i) and a patient having protein C deficiency (lines e and j). The results are shown in FIG. 12 and Table 11.

TABLE 11

| | NP series 16/12, series 1-5 | | | |
|---|---|---|---|---|
| | NP Ctad | F5 het | F2 het | PS |
| Lag Time Trombin Generation | 4.5 | 4.0 | 4.0 | 3.5 |
| Time To Trombin Peak | 11.5 | 7.5 | 7.5 | 6.5 |
| Trombin Peak Height | 141 | 246 | 343 | 209 |
| Trombin Potential (ETP) | 1967 | 2354 | 2618 | 1924 |
| ETP, procoagulant | 339 | 399 | 592 | 351 |
| ETP, anticoagulant | 1628 | 1955 | 2026 | 1573 |
| Plasmin Droptime | 9.0 | 4.0 | 4.0 | 3.5 |
| Plasmin Peaktime | 29.5 | 34.5 | 38.5 | 33.5 |
| Fibrin Lysis Time | 20.5 | 30.5 | 34.5 | 30.0 |
| Plasmin Peak Height | 627 | 601 | 506 | 539 |
| (PPeakHeight – PDropHeight)/FLT | 31.3 | 20.0 | 12.6 | 16.7 |
| Plasmin Potential, accel-phase | 6151 | 5524 | 4612 | 4384 |
| Plasmin Potential, PPT + 10 min | 6923 | 6140 | 6333 | 5776 |

Interestingly, all thrombophilia patients have a decreased thrombin generation lag time, increased total thrombin generation (thrombin potential) and interestingly decreased plasmin generation, resulting in an increased clot lysis time. The explanation might be more TAFI activation and due to this a delayed plasmin generation. After a while the activity of TAFI is gone and normal plasmin generation occurs.

Various modifications and variations of the described methods and assays of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the claims

I claim:

1. An in vitro method for determining thrombin potential and plasmin potential generated in a single enzymatic reaction mixture in a single well, the method comprising:
   adding (i) a trigger molecule for inducing thrombin generation;
   (ii) a thrombin-specific substrate, which, upon cleavage by thrombin, produces a measurable, thrombin-specific signal;
   (iii) a trigger molecule for inducing plasmin generation;
   (iv) a plasmin-specific substrate, which, upon cleavage by plasmin, produces a measurable, plasmin-specific signal;
   (v) a phospholipid-containing surface; and
   (vi) calcium ions;
   to a test sample comprising a blood product, thereby generating the single enzymatic reaction mixture;
   simultaneously measuring thrombin-specific and plasmin-specific signals in the single enzymatic reaction mixture in the single well; and
   determining the thrombin potential and the plasmin potential generated in the single enzymatic reaction mixture in the single well.

2. The method as claimed in claim 1, wherein the blood product is selected from the group consisting of plasma, drain fluid, whole blood and platelet-rich plasma.

3. The method as claimed in claim 1, wherein the trigger molecule for inducing thrombin generation is an initiator of the extrinsic pathway or an initiator of the intrinsic pathway.

4. The method as claimed in claim 3, wherein the initiator of the extrinsic pathway is tissue factor (TF).

5. The method as claimed in claim 3, wherein the initiator of the intrinsic pathway is glass, kaolin, or an acid.

6. The method as claimed in claim 1, wherein the trigger molecule for inducing plasmin generation is selected from the group consisting of urokinase, streptokinase and tissue plasminogen activator (tPA).

7. The method as claimed in claim 1, wherein the thrombin-specific substrate and/or the plasmin-specific substrate is a compound which, upon contact with thrombin and/or plasmin, respectively, releases a measurable group.

8. The method as claimed in claim 1, wherein the thrombin-specific substrate and the plasmin-specific substrate are fluorescent substrates.

9. The method as claimed in claim 8, wherein the substrates have different excitation and emission spectra.

10. The method as claimed in claim 9, wherein the thrombin-specific substrate is coupled to 7-amino-4-methylcoumarin.

11. The method as claimed in claim 10, wherein the thrombin-specific substrate is Bz-β-Ala-Gly-Arg-AMC-AcOH.

12. The method as claimed in claim 9, wherein the plasmin-specific substrate is coupled to rhodamine 110.

13. The method as claimed in claim 12, wherein the plasmin-specific substrate is (bis-(CBZ-L-phenylalanyl-L-arginine amide)).

14. The method as claimed in claim 1, wherein the phospholipid-containing surface is selected from the group consisting of cephalin, cells, viruses, and microvessels.

15. The method as claimed in claim 14, wherein the cells are endothelial cells, blood platelets, bacteria, or matrices of endothelial cells.

16. An in vitro method for determining the effect of a drug, protein, cell or other additive on thrombin potential and plasmin potential in a single enzymatic reaction mixture in a single well, the method comprising:
a) adding (i) a trigger molecule for inducing thrombin generation;
(ii) a thrombin-specific substrate, which, upon cleavage by thrombin, produces a measurable, thrombin-specific signal;
(iii) a trigger molecule for inducing plasmin generation;
(iv) a plasmin-specific substrate, which, upon cleavage by plasmin, produces a measurable, plasmin-specific signal;
(v) a phospholipid-containing surface; and
(vi) calcium ions;
to a test sample comprising a blood product, thereby generating a first single enzymatic reaction mixture;
simultaneously measuring thrombin-specific and plasmin-specific signals in the first single enzymatic reaction mixture in a single well;
b) adding (i) a trigger molecule for inducing thrombin generation;
(ii) a thrombin-specific substrate, which, upon cleavage by thrombin, produces a measurable, thrombin-specific signal;
(iii) a trigger molecule for inducing plasmin generation;
(iv) a plasmin-specific substrate, which, upon cleavage by plasmin, produces a measurable, plasmin-specific signal;
(v) a phospholipid-containing surface;
(vi) calcium ions; and
(vii) the drug, protein, cell or other additive
to a test sample comprising a blood product, thereby generating a second single enzymatic reaction mixture;
simultaneously measuring thrombin-specific and plasmin-specific signals in the second single enzymatic reaction mixture in a single well; and
c) comparing the thrombin-specific and plasmin-specific signals in the first single enzymatic reaction mixture with the thrombin-specific and plasmin-specific signals in the second single enzymatic reaction mixture;
thereby determining the effect of the drug, protein, cell or other additive on thrombin potential and plasmin potential in the second reaction mixture.

17. A kit for performing an in vitro hemostasis assay for measuring thrombin potential and plasmin potential comprising a single container comprising: a trigger molecule for inducing thrombin generation, a thrombin-specific substrate which, upon cleavage by thrombin, produces a measurable thrombin-specific signal, a plasmin-specific substrate which, upon cleavage by plasmin, produces a measurable plasmin-specific signal, a trigger molecule for inducing plasmin generation, a phospholipid-containing surface, and calcium ions.

18. The kit as claimed in claim 17, wherein the trigger molecule for inducing thrombin generation is an initiator of the extrinsic pathway.

19. The kit as claimed in claim 18, wherein the initiator of the extrinsic pathway is tissue factor (TF).

20. The kit as claimed in claim 17, wherein the trigger molecule for inducing plasmin generation is selected from the group consisting of urokinase, streptokinase, and tissue plasminogen activator (tPA).

21. The kit as claimed in claim 17, wherein the thrombin-specific substrate and/or the plasmin-specific substrate is a compound which, upon contact with thrombin and/or plasmin, respectively, releases a measurable group.

22. The kit as claimed in claim 17, wherein the thrombin-specific substrate and the plasmin-specific substrate are fluorescent substrates.

23. The kit as claimed in claim 22, wherein the substrates have different excitation and emission spectra.

24. The kit as claimed in claim 23, wherein the thrombin-specific substrate is coupled to 7-amino-4-methylcoumarin.

25. The kit as claimed in claim 24, wherein the thrombin-specific substrate is Bz-B¬Ala-Gly-Arg-AMC-AcOH.

26. The kit as claimed in claim 23, wherein the plasmin-specific substrate is coupled to rhodamine 110.

27. The kit as claimed in claim 26, wherein the plasmin-specific substrate is (bis¬(CBZ-L-phenylalanyl-L-arginine amide)).

* * * * *